US008052982B2

(12) United States Patent
Trigg et al.

(10) Patent No.: US 8,052,982 B2
(45) Date of Patent: *Nov. 8, 2011

(54) BIOIMPLANT FORMULATION COMPRISING LECITHIN AND STEARIN

(75) Inventors: Timothy Elliott Trigg, Warrawee (AU); John Desmond Walsh, Curl Curl (AU); Deborah Ann Rathjen, Flagstaff Hill (AU)

(73) Assignee: Peptech Animal Health PTY Limited, New South Wales (AU)

( * ) Notice: Subject to any disclaimer, the term of this patent is extended or adjusted under 35 U.S.C. 154(b) by 1260 days.

This patent is subject to a terminal disclaimer.

(21) Appl. No.: 11/727,655

(22) Filed: Mar. 27, 2007

(65) Prior Publication Data

US 2008/0031956 A1 Feb. 7, 2008

Related U.S. Application Data

(63) Continuation-in-part of application No. 11/041,270, filed on Jan. 25, 2005, now abandoned, which is a continuation of application No. 09/743,059, filed as application No. PCT/AU99/00585 on Jul. 20, 1999, now Pat. No. 6,913,761.

(30) Foreign Application Priority Data

Jul. 20, 1998 (AU) .................................. PP4730
Jul. 20, 1998 (AU) .................................. PP4731
May 13, 1999 (AU) .................................. PQ324

(51) Int. Cl.
*A61K 9/00* (2006.01)

(52) U.S. Cl. .................................................. 424/400
(58) Field of Classification Search .................. None
See application file for complete search history.

(56) References Cited

U.S. PATENT DOCUMENTS

| 4,578,391 A | 3/1986 | Kawata et al. |
| 4,981,681 A | 1/1991 | Tosti |
| 6,337,318 B1 * | 1/2002 | Trigg et al. .................. 514/10.3 |
| 6,913,761 B1 * | 7/2005 | Trigg et al. .................. 424/423 |

FOREIGN PATENT DOCUMENTS

| EP | 0 353 045 A2 | 1/1990 |
| EP | 0 523 330 B1 | 4/1992 |
| EP | 0 523 330 A1 | 1/1993 |
| GB | 2 167 662 A | 6/1986 |
| JP | 9-104626 A | 4/1997 |
| WO | WO 91/05548 | 5/1991 |
| WO | WO 91/07171 | 5/1991 |
| WO | WO 94/08623 | 4/1994 |
| WO | WO 96/40049 A1 | 12/1996 |
| WO | WO 97/00693 * | 1/1997 |
| WO | WO 97/03634 A1 | 2/1997 |
| WO | WO 97/15285 | 5/1997 |
| WO | WO 98/02146 A2 | 1/1998 |
| WO | WO 98/08533 | 3/1998 |
| WO | WO 99/48500 | 9/1999 |

* cited by examiner

*Primary Examiner* — Carlos Azpuru
(74) *Attorney, Agent, or Firm* — Nixon & Vanderhye

(57) ABSTRACT

Pharmaceutical and/or veterinary formulation containing about 2-30% (w/w) (on an active basis) of at least one active agent, about 0.5-20.0% (w/w) of a pore-forming agent comprising lecithin and an organic salt, and the balance stearin.

17 Claims, 12 Drawing Sheets

BIOIMPLANT FORMULATION COMPRISING LECITHIN AND STEARIN

Figure 1:
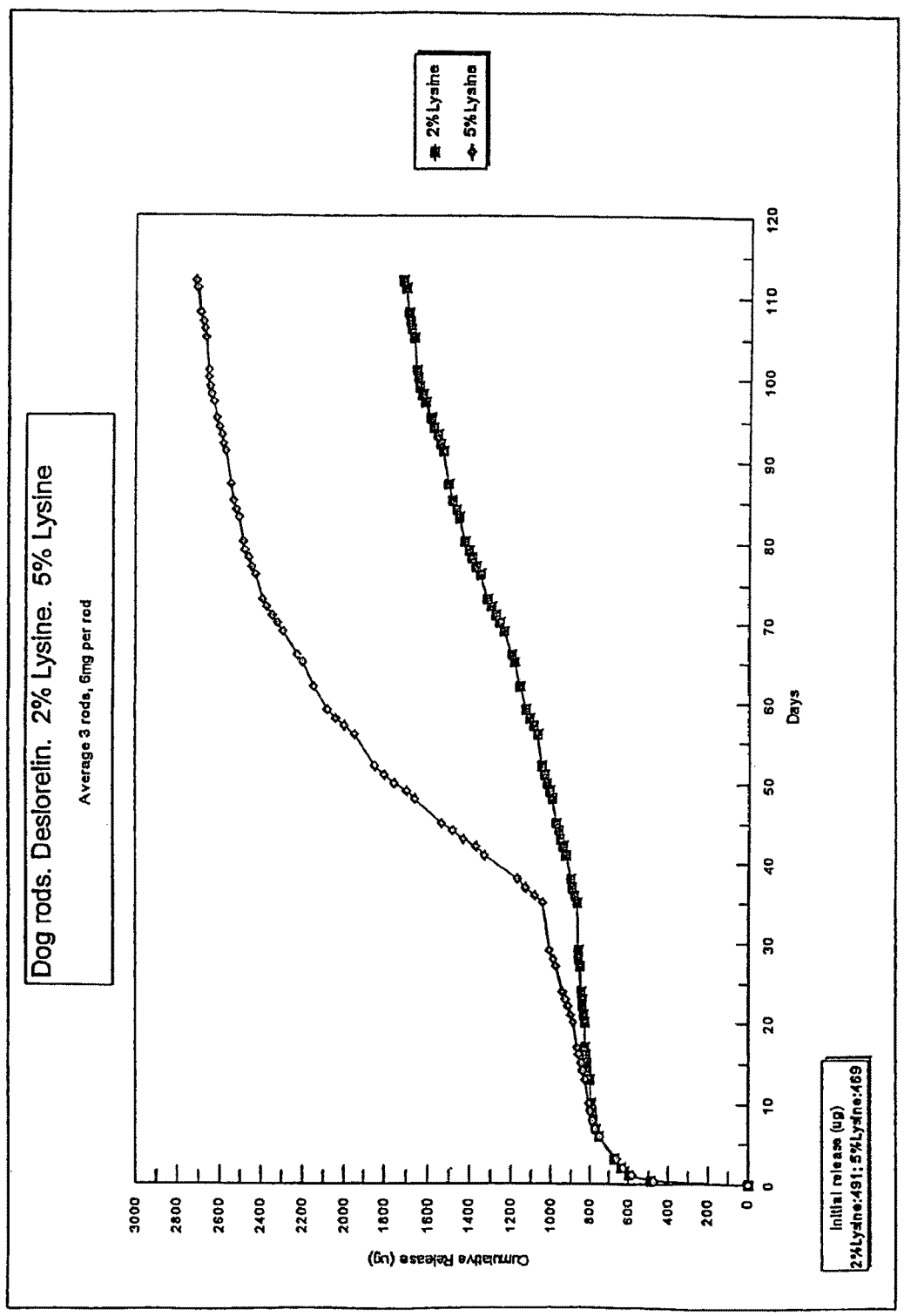

This application is a continuation-in-part of application Ser. No. 11/041,270, filed Jan. 25, 2005, now abandoned which is a continuation of application Ser. No. 09/743,059, filed Feb. 12, 2001, now U.S. Pat. No. 6,913,761 which is a 371 of PCT/AU99/00585, filed Jul. 20, 1999, the entire content of which is hereby incorporated by reference in this application.

FIELD OF THE INVENTION

The present invention relates to pharmaceutical and/or veterinary formulations for the sustained release of at least one active agent. Preferred active agents include gonadotropin-releasing hormone (GnRH) agonists (e.g. deslorelin), GnRH antagonists (e.g. cetrorelix), somatostatin analogues (e.g. somatostatin-14 and octreotide), lipid lowering agents (e.g. simvastatin), cyclosporins (e.g. cyclosporin A), angiotensin converting-enzyme inhibitors (e.g. captopril), calcitonins, substance P antagonists, painkillers (e.g. morphine), opioid antagonists (e.g. naltrexone), anti-depressants (e.g. venlafaxine) and non-steroidal anti-inflammatory agents (e.g. naproxen sodium).

BACKGROUND OF THE INVENTION

For reasons including improved efficacy of action and reduced frequency of administration, there is considerable interest in the development of pharmaceutical and veterinary formulations capable of controllably releasing active agents for sustained periods (e.g. up to 6 months or more). Types of pharmaceutical agents that would particularly benefit from the development of such formulations are those which are typically administered by patients themselves over long periods (e.g. insulin for diabetes treatment, and gonadotropin-releasing hormone (GnRH) agonists for reproductive control and treatment of sex hormone-dependent diseases and conditions) and require high levels of patient compliance. In the veterinary context, sustained release formulations would reduce the stress often caused to the animal and veterinarian/owner alike by the need for repeated administration of active agents.

The present applicant's have found that sustained release of at least one active agent in humans and other animals for periods of 7 days up to about 2 years, can be achieved by using a solid formulation comprising stearin as an excipient in combination with a substance which, while not wishing to be bound by theory, appears to form pores and/or cracks in the excipient to enable the release of the active agent(s).

SUMMARY OF THE INVENTION

Thus, in a first aspect, the present invention provides a pharmaceutical and/or veterinary formulation comprising about 2-30% (w/w) (on an active basis) of at least one active agent, about 0.5-20.0% (w/w) of a pore-forming agent comprising lecithin and an organic salt, and the balance stearin.

In a preferred embodiment, the formulation comprises about 5-10% (w/w) (on an active basis) of at least one active agent, about 1.0-10.0% (w/w) of a pore-forming agent comprising lecithin and an organic salt, and the balance stearin.

In a more preferred embodiment, the formulation comprises about 5-10% (w/w) (on an active basis) of at least one active agent, about 2.0-5.0% (w/w) of a pore-forming agent comprising lecithin and an organic salt, and the balance stearin.

In a second aspect, the present invention provides a method of treating a disease or condition in a human or other animal, the method comprising administering to the human or other animal the formulation of the first aspect of the invention.

DETAILED DISCLOSURE OF THE INVENTION

The at least one active agent utilised in the formulation of the present invention, may be selected from agents having pharmaceutical or veterinary significance and may be any or a combination of peptides (e.g. hormones and antigens), polypeptides and proteins, and nucleic acid compounds and derivatives such as DNA and RNA.

Preferred active agents include:

(1) GnRH Agonists

Particularly preferred GnRH peptide agonists are deslorelin (described in U.S. Pat. No. 4,218,439), eulexin (described in FR7923545, WO 86/01105 and PT100899), goserelin (described in U.S. Pat. No. 4,100,274, U.S. Pat. No. 4,128,638, GB9112859 and GB9112825), leuprolide (described in U.S. Pat. No. 4,490,291, U.S. Pat. No. 3,972,859, U.S. Pat. No. 4,008,209, U.S. Pat. No. 4,005,063, DE2509783 and U.S. Pat. No. 4,992,421), dioxalan derivatives such as are described in EP 413209, triptorelin (described in U.S. Pat. No. 4,010,125, U.S. Pat. No. 4,018,726, U.S. Pat. No. 4,024,121, EP 364819 and U.S. Pat. No. 5,258,492), meterelin (described in EP 23904), buserelin (described in U.S. Pat. No. 4,003,884, U.S. Pat. No. 4,118,483 and U.S. Pat. No. 4,275,001), histrelin (described in EP217659), nafarelin (described in U.S. Pat. No. 4,234,571, WO93/15722 and EP52510), lutrelin (described in U.S. Pat. No. 4,089,946), leuprorelin (described in Plosker et al., Drugs 48 930-967, 1994) and LHRH analogues such as are described in EP181236, U.S. Pat. No. 4,608,251, U.S. Pat. No. 4,656,247, U.S. Pat. No. 4,642,332, U.S. Pat. No. 4,010,149, U.S. Pat. No. 3,992,365 and U.S. Pat. No. 4,010,149. The disclosures of each the patent specifications and papers referred to above are incorporated herein by reference.

The most preferred GnRH agonists are goserelin, deslorelin, leuprorelin, triptorelin, meterelin, buserelin, histrelin, nafarelin and combinations thereof. The formulae of these compounds are provided below:

| | |
|---|---|
| Goserelin | $C_{59}H_{84}N_{18}O_{14}C_2H_4O_2$<br>D-Ser(Bu$^t$)$^6$Azgly$^{10}$-LHRH Acetate<br>3-[5-oxo-L-prolyl-L-tryptophyl-L-seryl-L-tyrosyl-(3-O-tert-butyl)-D-seryl-L-leucyl-L-arginyl-L-prolyl]<br>cabazamide acetate (SEQ ID NO: 1). |
| Deslorelin | 6-D-tryptophan-9-(N-ethyl-L prolinamide)-10-deglycinamide<br>P Glutamine-Histidine-Tryptophan-Serine-Tyrosine-D Tryptophan-Leucine-Arginine-Proline-ethylamide<br>(SEQ ID NO: 2). |
| Leuprorelin | $C_{59}H_{84}N_{16}O_{12}$, $C_2H_4O_2$<br>Leuprorelin Acetate<br>5-oxo-L-prolyl-L-histidyl-L-tryptophyl-L-seryl-L-tyrosyl-D-leucyl-L-arginyl-N-ethyl-L-prolinamide acetate<br>(SEQ ID NO: 3). |
| Triptorelin | $C_{59}H_{84}N_{16}O_{12}$, $C_2H_4O_2$<br>D-Trp$^6$-LHRH<br>5-oxo-L-prolyl-L-histidyl-L-tryptophyl-L-seryl-L-tyrosyl-D-tryptophyl-L-leucyl-L-arginyl-L-prolylglycinamide<br>(SEQ ID NO: 4). |
| Meterelin | Des Gly$^{10}$-2-methyl-D-Trp$^6$-Pro-ethyl-amide$^9$ LHRH<br>(SEQ ID NO: 5). |

| | |
|---|---|
| Buserelin | $C_{60}H_{86}N_{16}O_{13}, C_2H_4O_2$<br>D-Ser(Bu$^t$)$^6$-Pro9-NEt LHRH Acetate<br>Oxo-L-prolyl-L-histidyl L-tryptophyl-L-seryl-L-tyrosyl-O-tert-butyl-D-seryl-L-leucyl-L-arginyl-N-ethyl-L-prolinamide acetate (SEQ ID NO: 6). |
| Histrelin | Pro-His-Trp-Ser-Tyr-Leu-D(N-benzyl) His-Arg-Pro-N-ethylamide (SEQ ID NO: 7). |
| Nafarelin | $C_{66}H_{83}N_{17}O_{13}, xC_2H_4O_2yH_2O$Oxo-L-prolyl-L-histidyl-L-tryptophyl-L-seryl-L-tyrosyl-3-(2-naphthyl)-D-alanyl-L-leucyl-L-arginyl-N-ethyl-L-prolylglycinaminde acetate hydrate (SEQ ID NO: 8). |

Formulations according to the invention which include a GnRH agonist as the at least one active agent may be used for controlling reproductive function or for the treatment of any disease or condition wherein reduction of sex hormone (i.e. testosterone or estradiol) levels over a prolonged period is beneficial. Examples include prostrate cancer, ovarian and breast cancer, benign hormone-dependent disorders such as endometriosis, myoma and premenstrual tension, uterine fibroids, induction of endometrial atrophy prior to surgery, suppression of germ cell activity in chemotherapy, hirsutism, cyclic auditory dysfunction, porphyria and precocious puberty in children, benign prostatic hypertension in dogs and for use in other conditions where castration is known to have a beneficial clinical effect, including restoration of T cell-mediated immunity.

(2) GnRH Antagonists

Particularly preferred GnRH antagonists are ramorelix (L-prolone,1-(N2-(N—(N—(N—(N—(N—(N—(N-acetyl-3-(2-naphhthalenyl)-D-alanyl)-4-chloro-D-phenylalanyl)-D-tryptophyl)-L-seryl)-L-tyrosyl-O-(6-deoxy-alpha-L-mannopyranosyl)-D-seryl)-L-leucyl)-L-arginyl)-2-(aminoacrbonyl) hyrazide, teverelix (D-alaninamide,N-acetyl-3-(2-naphthalenyl)-D-alayl-4-chloro-D-phenylalanyl-3-(3-pyridinyl)-D-alanyl-L-seryl-L-tyrosyl-N6-(aminocarbonyl)-D-lysyl-L-leucyl-N6-(1-methylethyl)-L-lysyl-L-prolyl, cetrorelix (D-Alaninamode, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl, ganirelix (N—Ac-D-Nal,D-pCl-Phe,D-Pal,DhArg(Et)2,hArg(Et)2,D-Ala) GnRH, alanex, abarelix (D-Alaninamide,N-acetyl-3-(2-naphthalenyl)-D-alanyl-4-chloro-D-phenylalanyl-3-(3-pyridinyl)-D-alanyl-L-seryl-N-methyl-L-tyrosyl-D-asparainyl-L-leucyl-N6-(1-methylethyl)-L-lysyl-L-prolyl; N—(S)-tetrahydrofuroyl-Gly-D2Nal-D4Ciphe-D3Pal-Ser-NmeTyr-D-lys(Nic)-Leu-Lys(Isp)-Pro-D-Ala-NH2; isopropyl-13-(N-benzyl-N-methaminomethyl)-7-(2,6-diflurobenzyl)-4,7-dihydro-2-(4-isobutyrylaminophenyl)-4-oxothieno(2,3-b)pyridine-5-carboxyatehydrochloride). Other preferred GnRH antagonists are described in U.S. Pat. No. 5,110,904, U.S. Pat. No. 5,300,492, U.S. Pat. No. 5,807,983, U.S. Pat. No. 5,169,932, U.S. Pat. No. 5,296,468 and U.S. Pat. No. 5,502,035.

(3) Somatostatin Analogues

Particularly preferred somatostatin analogues include somatostatin-14, octreotide, lanreotide and angiopeptin cyclopeptides (U.S. Pat. No. 5,569,647).

Formulations according to the invention which include a somatostatin analogue as the at least one active agent may be used for treating, for example, hyperinsulinaemia and peptic ulcers.

(4) Lipid Lowering Agents

Particularly preferred lipid lowering agents include compounds which inhibit HMG CoA reductase such as cerevastatin, mevastatin, simvastatin, pravastatin and lovastatin. Formulations according to the invention which includes these agents may be used for treating, for example, hyperlipoproteineamia.

(5) Cyclosporins

Preferred cyclosporins include naturally occurring cyclosporins (e.g. as described by Dreyfuss et al., (1976) Europ. J. Appl. Microbiol. Vol. 3:125-133), and analogues (e.g. as described by Wenger R. M. (1982), Chemistry of Cyclosporin A in "Cyclosporin" A", White D. G. G. ed., Amsterdam; Elsevier).

Formulations according to the invention which include a cyclosporin or cyclosporin analogue as the at least one active agent may be used, for example, as immunosuppressive agents for prophylaxis and treatment of organ rejection in allogeneic transplants.

(6) Angiotensin Converting Enzyme Inhibitors

Preferred ACE inhibitors include captopril, enalapril, trandolaprilate, perindoprilate, quinaprilate, fasidotril, omapatrilate and lisinopril.

Formulations according to the invention which include such agents may be used, for example, as antihypertensives.

(7) Calcitonins

Preferred calcitonins include human, salmon, and porcine calcitonin. Analogues of these polypeptides may also be suitable.

Formulations according to the invention which include calcitonin or calcitonin analogues may be used for treatment of, for example, hypercalcemia and for decreasing concentrations of phosphate in patients suffering from hyperparathyroidism, vitamin D intoxication, and osteolytic bone metastases.

(8) Substance P Antagonists

Preferred substance P antagonists include fragment 4-11 (i.e. Pro-Gln-Gln-Phe-Phe-Gly-Leu-Met-NH$_2$ (SEQ ID NO:9) and variant forms), fragment 5-11 (i.e. Gln-Gln-Phe-Phe-Gly-Leu-Met-NH$_2$ (SEQ ID NO:10) and variant forms), fragment 6-11 (i.e. Gln-Phe-Phe-Gly-Leu-Met-NH$_2$ (SEQ ID NO:11) and variant forms), fragment 7-11 (i.e. Phe-Phe-Gly-Leu-Met-NH$_2$ (SEQ ID NO:12)), fragment 8-11 (i.e. Phe-Gly-Leu-Met-NH$_2$ (SEQ ID NO:13)) and fragment 9-11 (i.e. Gly-Leu-Met-NH$_2$ (SEQ ID NO:14)). Other suitable substance P antagonists include those described in the present applicant's co-pending Australian Provisional Patent Application No. PP9008.

Formulations according to the invention which include substance P antagonists may be used for treatment of cancer including chemotherapy-induced nausea and vomiting, pain, allergy, asthma, inflammatory conditions including inflammatory bowel disease and depression.

(9) Painkillers

Preferred painkillers include opioids such as morphine, levorphanol and meperidine (pethidine), and amide local anaesthetics such as bupivacaine, lidocaine, etidocaine and mepivacaine.

Formulations according to the invention which include such painkilling agents may be used to treat acute pain (e.g. such as that experienced by hip replacement patients) or chronic regional pain.

(10) Opioid Antagonists

Preferred opioid antagonists include naltrexone, naloxone and methadone.

Formulations according to the invention which include opioid antagonists may be used for treatment of opioid dependency.

(11) Anti-Depressants

Preferred anti-depressants include venlafaxine, triflupromazine, methotrimeprazine, promethazine, buspirone, gepirone and fluoxetine (Prozac).

(12) Non-Steroidal Anti-Inflammatory Agents

Preferred non-steroidal anti-inflammatory agents include naproxen sodium indomethacin, sulindac, tolmelin, acemetacin, zomepirac, mefenamic acid, fenoprofen, flufenamic acid, phenylbutazone, flurbiprofen, ketoprofen and axsain.

Formulations according to the invention which include non-steroidal anti-inflammatory agents may be used for the treatment of post-operative inflammation and inflammation associated with, for example, rheumatoid arthritis.

(13) Miscellaneous

Other suitable active agents include paroxetine for treatment of social anxiety disorder/social phobia, galanin antagonists such as galanin fragment 1-13-Pro-Pro-Ala-Leu-Ala-Leu-Ala amide (SEQ ID NO:15) and galanin (1-13)-spantide 1 for treatment of obesity, eating disorders, depression and pain; activin and inhibin fragments such as I-subunit fragment 1-32 and σ-fragment 67-94 for fertility control; adrenocorticotropic hormone (ACTH) and variants and fragments for treatment of West Syndrome and infantile spasms; growth hormone and its analogues for replacement therapy in growth-hormone deficient children; erythropoietin (EPO) and its analogues for treatment of anaemia; endothelin antagonists for prevention of congestive heart failure, prevention of acute renal failure and subarachnoid haemorrhage, prevention and treatment of atherosclerosis, treatment of hypertension, prevention of stroke and treatment of chronic obstructive pulmonary disease; leptin and its agonists and antagonists for treatment of obesity and eating disorders such as anorexia nervosa, and for weight loss; thyrotropin releasing hormone (TRH) and its analogues (e.g. pGlu-His-Pro-Gly (SEQ ID NO:16)) for treatment of, for example, epilepsy; and theophylline and its analogues for the treatment of asthma, systemic capillary leak syndrome and Parkinson's disease. Vaccine antigens, including DNA encoding vaccine antigens, may also be delivered in a formulation according to the present invention.

Formulations according to the invention may include a combination of active agents. Examples of preferred combinations (comprising "Agent 1" and "Agent 2") are shown in Table 1.

TABLE 1

| Agent 1 | Agent 2 |
|---|---|
| HMG Co A reductase inhibitor | Gemfibrozil |
| Non-steroidal anti-inflammatory agent | Mycophenolate mofelil |
| GnRH agonist | Trk tyrosine inhibitor |
| GnRH agonist | Testosterone |
| Calcitonin | Estrogen |
| Calcitonin | Etridonate |
| Calcitonin | Pamridonate |
| Octreotide | α-interferon |
| Octreotide | IGF-1 |
| Octreotide | Miclodrine |
| GnRH agonist | Flutamide |
| Etofylline | Theophylline |

Preferably, the at least one active agent is/are of low to moderate lipophilicity. More preferably, at least one active agent has a log octanol/water partition coefficient (log P) (Ruelle and Kesselring (1998), J Pharm Sci. Vol. 87:1115-24) in the range of 5.0 to −3.0. Most preferred are active agents having a log P value in the range of 3.0 to −3.0 and, particularly, those having a log P value in the range of 1.0 to −3.0.

Log P values for representatives of the abovementioned classes of active agents are provided in Table 2.

TABLE 2

| Agent | log octanol/water partition (log P) |
|---|---|
| octreotide | 1.40 |
| cyclosporin A | 2.90 |
| captopril | −1.86 |
| trandolaprilate | 1.02 |
| perindoprilate | −0.36 |
| quinaprilate | 0.69 |
| morphine | 0.76 |
| lidocaine | 2.26 |
| methadone | 3.93 |
| promethazine | 4.75 |
| indomethacin | 4.27 |
| flufenamic acid | 1.14 |
| phenylbutazone | 3.16 |
| theophylline | −0.02 |
| etofylline | 0.35 |
| TRH | −2.40 |

Preferably, the at least one active agent is/are an agent(s) other than a nucleic acid compound or a derivative.

The pore-forming agent comprises a combination of lecithin and an organic salt which enables the sustained release of the at least one active agent from the stearin excipient.

Lecithin is a mixture of diglycerides of stearic, palmitic and oleic acids linked to the choline ester of phosphoric acid. The efficacy of lecithin as a pore-forming agent in a sustained release formulation comprising deslorelin and stearin is described in International patent application No. PCT/AU96/00370 (WO 97/00693), the entire disclosure of which is incorporated herein by reference.

Preferably, the organic salt is selected from acetates, formates, propionates, glutamates, and aspartates. More preferably, the organic salt is sodium acetate.

As will be evident from the examples herein, variation of the identity and/or amount of the pore-forming agent utilised allows for the manipulation of the release profile of the active agent(s) to suit particular therapeutic uses.

The stearin excipient is preferably in a non-crystalline form. Stearin comprises as the principal fatty acids, C16:0 (45%) and C18:0(53%). The melting point of stearin is about 60° C. It is believed that the use of stearin as the excipient contributes to the success of the formulations according to the invention, because it appears, surprisingly, to produce only a minimal to mild inflammatory response in a recipient resulting in the encapsulation of the formulation within a thin layer of fibroblasts.

It will be appreciated by persons skilled in the art, that alternative formulations comprising excipient(s) with similar characteristics to those included in the formulation defined above in the first aspect may likewise provoke minimal to mild inflammatory responses and consequently be useful for the sustained-release of an active agent(s). Such alternative formulations are to be regarded as falling within the scope of the present invention.

The formulations according to the invention may be for administration to humans and other animals selected from dogs, cats, other domestic animals, and captive wildlife.

Typically, the formulations will release the active agent(s), in vitro, into phosphate buffered saline (PBS: pH 7.3, prepared by dissolving 8.00 g of sodium chloride, 1.00 g disodium hydrogen phosphate anhydrous, 0.40 g sodium dihydrogen phosphate dihydrate (0.31 g if anydrous), and 0.05 g sodium azide in 1 litre of deionised water), at 37° C. at a rate of about 2-350 µg/day for at least 7 days and up to about 2 years.

Further, the formulations will typically exist as a depot formulation for example in the form of free flowing beads or rods which may have been extruded.

Extruded rods may be cut into predetermined lengths for implantation, by standard techniques, in a human or other animal. As will be readily appreciated, the length of the rod will determine the rate and dose of the active agent(s). As opposed to implanting longer rods more than one rod can be implanted in each human or other animal. Injection of a suspension of formulated particulate material such as free flowing beads may also deliver the active agent(s) at the desired rate and dose.

Formulations for administration as free flowing beads and/or implants, particularly to dogs, may be produced as follows:

Stearin (supplied as free flowing beads of 1 mm or less in diameter made by Vandenberg Foods) and pore-forming agent are mixed. The active agent may then be added and thoroughly mixed into the excipient and pore-forming agent mixture. This material may then be used for injection. Alternatively the mixture can be transferred to the barrel of a ram extruder that has a 1 mm nozzle attached and is equilibrated to 55° C. (or other temperature sufficient to soften the stearin). After attaching the ram, pressure (40 psi) is applied until the product begins to extrude. At this point the pressure can be backed off and the product allowed to reach 55° C. (or other temperature sufficient to soften the stearin). The product may then be extruded at, for example, a rate of 3 g over a 30 second period. The resulting extrudate is then allowed to cool and then broken up and re-extruded through a 1 mm nozzle to ensure uniformity of content throughout the mix. The 1 mm nozzle may then be replaced with a 2.3 mm diameter nozzle and the product extruded (using the same temperature equilibration procedure prior to extrusion). After cooling the long rods produced can be sectioned into lengths of the required weight and the sectioned lengths sterilised by gamma-irradiation.

Alternatively, formulations for administration as bioimplants, particularly for dogs, may be produced by:

Stearin and pore-forming agent are mixed. The active agent may then be added and thoroughly mixed into the excipient and pore-forming agent mixture. The mixture can then be transferred to the barrel of an extruder that has a 2.3 mm nozzle attached and which has been equilibrated to a temperature sufficient to soften the stearin. The extruder is started and the product begins to extrude and the extrudate is cut to length. The sectioned length can be terminally sterilised.

Further, in preparing formulations according to the present invention, especially where the at least one active agent is a peptide(s), polypeptide(s) or protein(s), it is preferred that the at least one active agent is firstly pre-treated with a process comprising at least two freeze drying steps. Such freeze drying steps may be conducted in accordance with any of the commonly known methods for freeze drying of proteinaceous materials. It is, however, preferred that the active agent(s) be freeze dried from a 5-50% (more preferably, 5-15%) (w/w) solution of the active agent(s) in a suitable solvent (e.g. an alcohol solution such as 30% (w/w) ethanol in water). The freeze dried active agent(s) may then be redissolved or homogenised in a suitable solvent (e.g. 25-75% (w/w) in a diluted weak acid solution such as 1-5% (w/w) acetic acid in water) and subsequently freeze dried again. Thus, the freeze drying of the active agent(s) may comprise the steps of;

(i) forming a 5-50% (w/w) solution of the active agent(s),
(ii) freeze drying said solution of step (i),
(iii) forming a 25-75% (w/w) solution or homogenate from said freeze dried active agent(s), and
(iv) freeze drying said solution or homogenate of step (iii).

The term "on an active basis" is to be given its usual meaning in the art. That is, it is used to indicate that the % amount (w/w) of peptide agonist or analogue present in a formulation is based on the dry weight of the peptide agonist or analogue.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by reference to the following, non-limiting examples and accompanying figures.

BRIEF DESCRIPTION OF THE ACCOMPANYING FIGURES

FIG. 1 provides a graph showing average daily in vitro release profiles from three 100 mg rods of each of formulations:
(I) 6% deslorelin, 2% lysine and balance stearin; and
(II) 6% deslorelin, 5% lysine and balance stearin.

The graph demonstrates an initial rapid release of the active agent and then continued release extending over a prolonged period (110 days).

Figure 2:
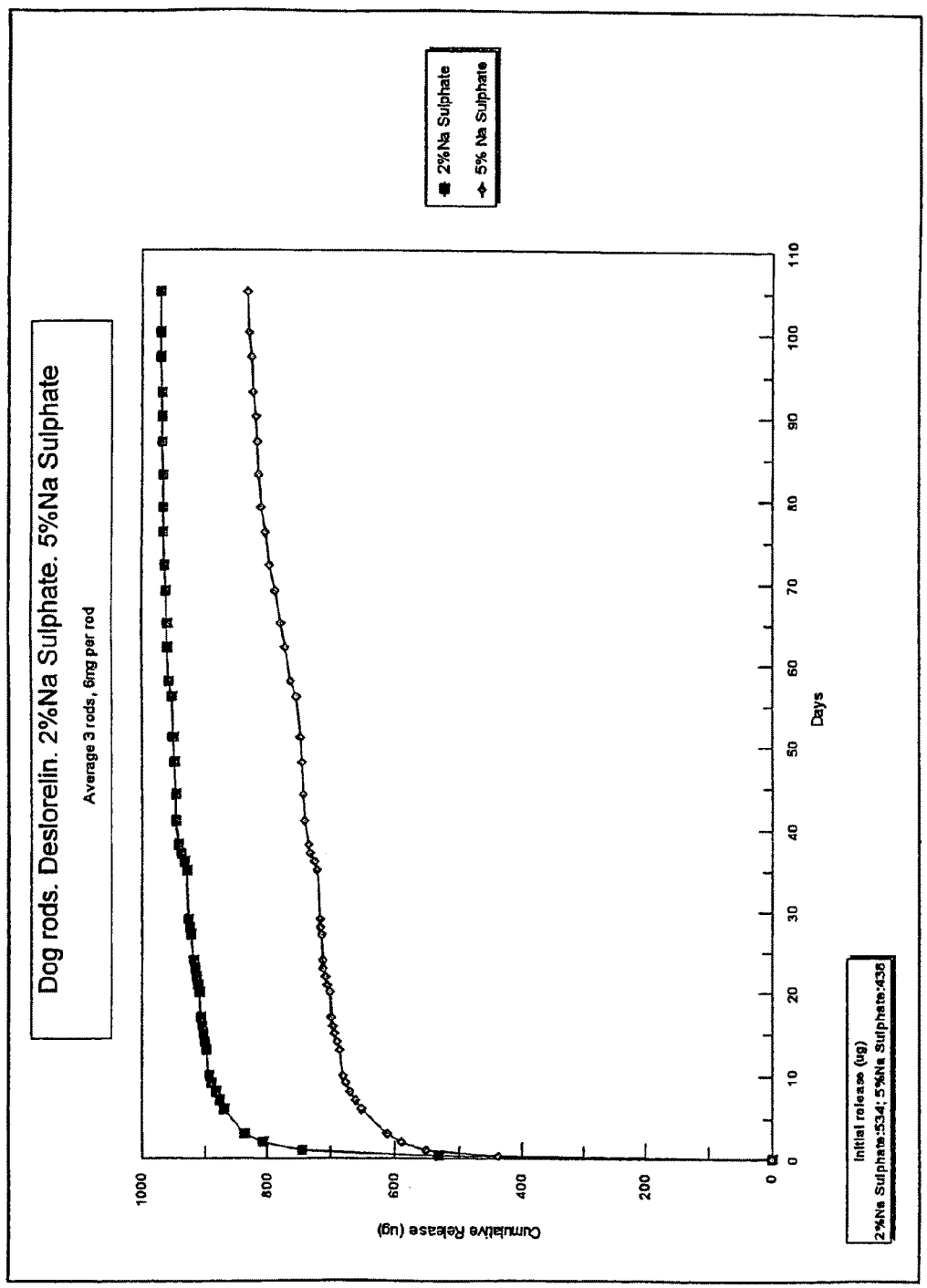

FIG. 2 provides a graph showing the average daily in vitro release profile from three 100 mg rods of each of formulations:
(III) 6% deslorelin, 2% sodium sulphate and balance stearin; and
(IV) 6% deslorelin, 5% sodium sulphate and balance stearin.

The graph demonstrates that a greater initial rapid release of deslorelin (534 µg vs. 438 µg) was achieved using 5% sodium sulphate. After the initial rapid release (finished at about day 10), the rate of release was about 10-2 µg/day for the next 95 days for both formulations.

Figure 3:
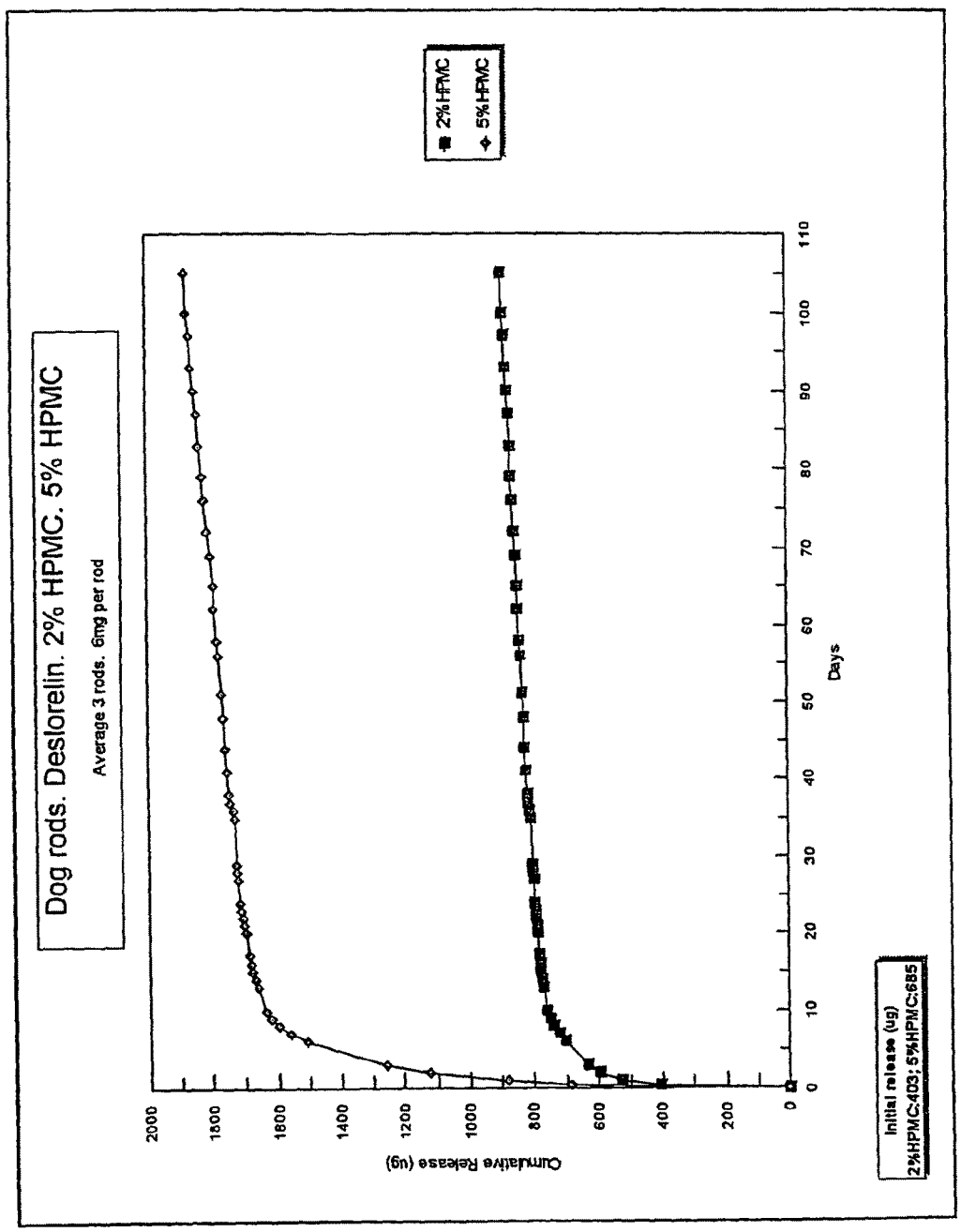

FIG. 3 provides a graph showing the average daily in vitro release profile from three 100 mg rods of each of formulations:
(V) 6% deslorelin, 2% hydroxy propyl methylcellulose (HPMC) and balance stearin; and
(VI) 6% deslorelin, 5% hydroxy propyl methylcellulose (HPMC) and balance stearin.

The graph demonstrates that a much greater initial rapid release of deslorelin (685 µg vs. 403 µg) was achieved using 5% HPMC. After the initial rapid release (finished at about day 10), the rate of release was about 10-2 µg/day for the next 95 days for both formulations.

Figure 4:
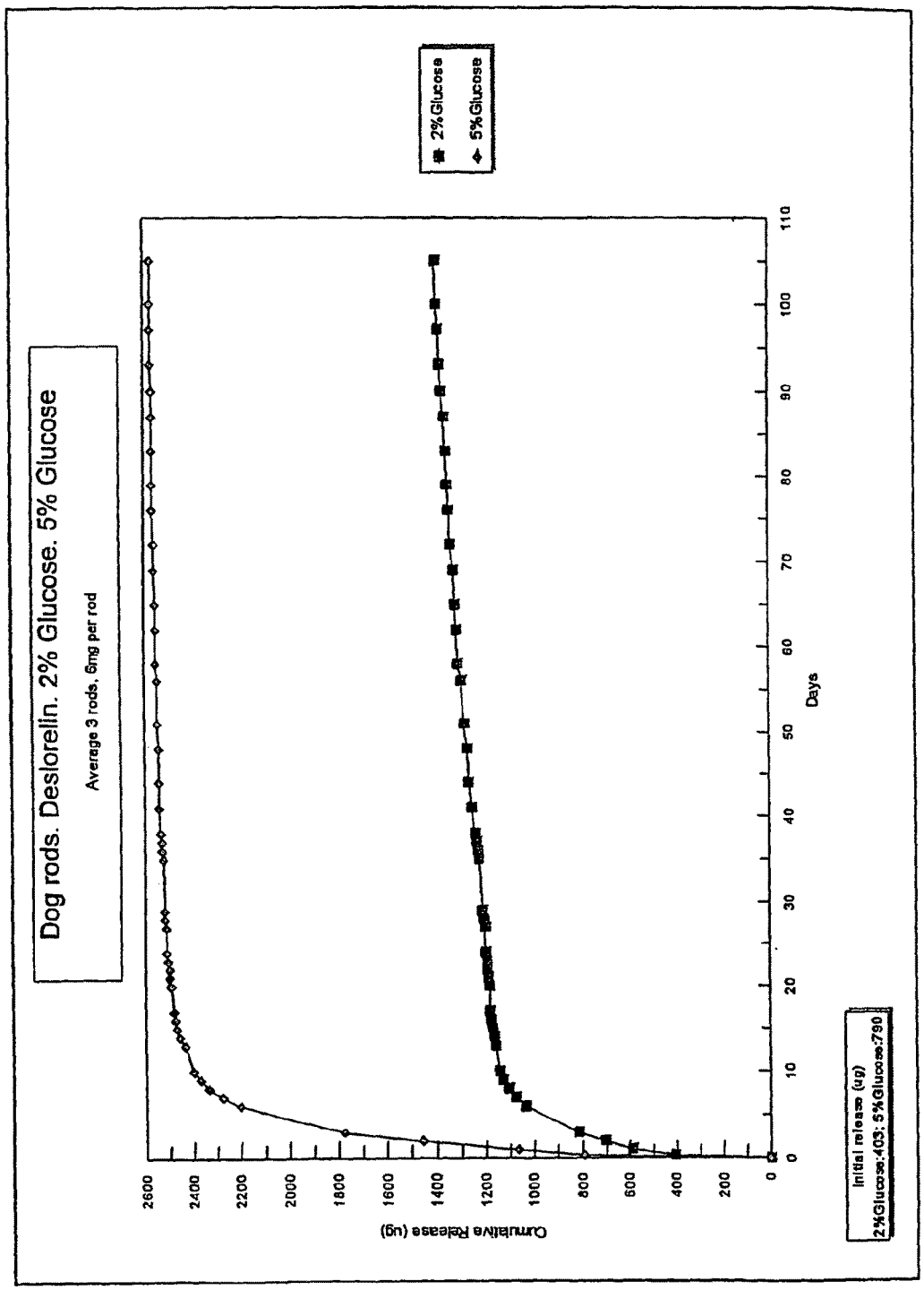

FIG. 4 provides a graph showing the average daily in vitro release profile from three 100 mg rods of each of formulations:
(VII) 6% deslorelin, 2% glucose and balance stearin; and
(VIII) 6% deslorelin, 5% glucose and balance stearin.

The graph demonstrates that a much greater initial rapid release of deslorelin (790 µg vs. 403 µg) was achieved using 5% glucose. After the initial rapid release (finished at about day 10), the rate of release was about 50-2 µg/day for the next 95 days for both formulations.

Figure 5:
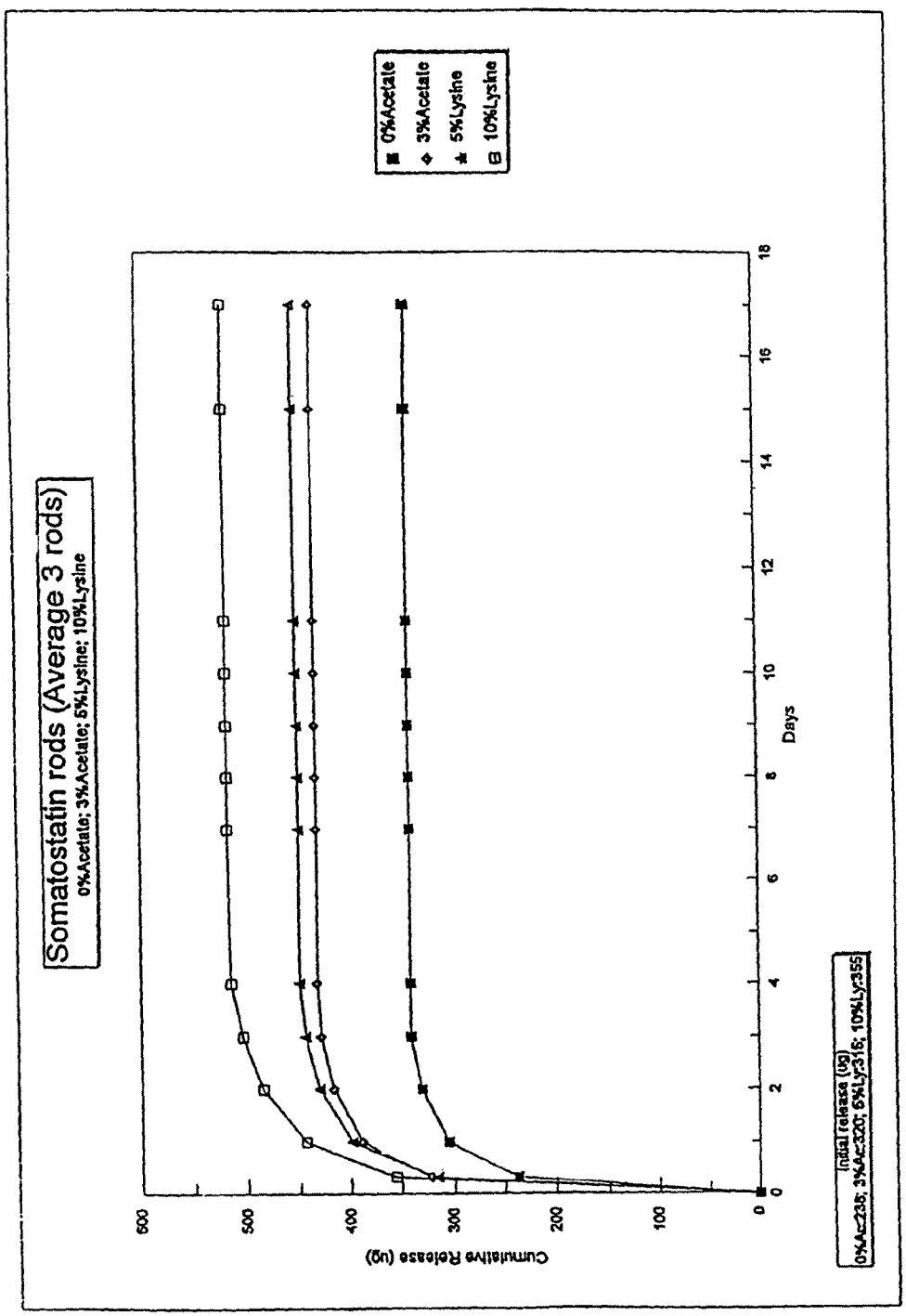

FIG. 5 provides a graph showing the average daily in vitro release profile from three 100 mg rods of each of formulations:

(IX) 6% somatostatin, and balance stearin;
(X) 6% somatostatin, 3% sodium acetate and balance stearin;
(XI) 6% somatostatin, 5% lysine and balance stearin; and
(XII) 6% somatostatin, 10% lysine and balance stearin.

The graph demonstrates that a greater initial rapid release of somatostatin was achieved using lysine than sodium acetate. After the initial rapid release (finished at about day 2), the rate of release in all cases slowed and plateaued by day 7.

Figure 6:
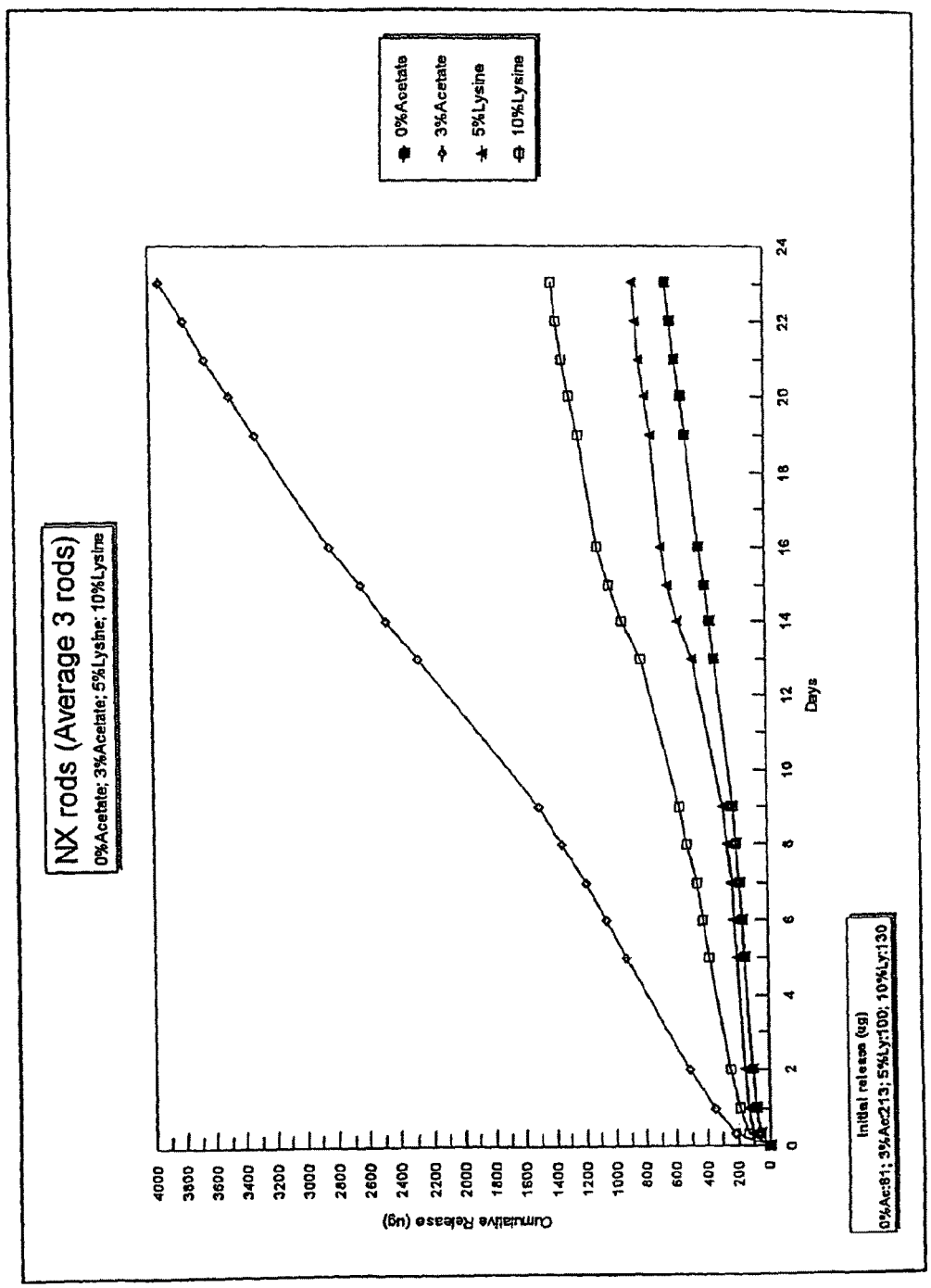

FIG. 6 provides a graph showing the average daily in vitro release profile from three 100 mg rods of each of formulations:

(XIII) 6% naltrexone (NX), and balance stearin;
(XIV) 6% naltrexone (NX), 3% sodium acetate and balance stearin;
(XV) 6% naltrexone (NX), 5% lysine and balance stearin; and
(XVI) 6% naltrexone (NX), 10% lysine and balance stearin.

The graph demonstrates that a sustained gradual release of naltrexone was achieved by all formulations over 23 days of testing, although the average daily release was low when no sodium acetate or lysine was included.

Figure 7:
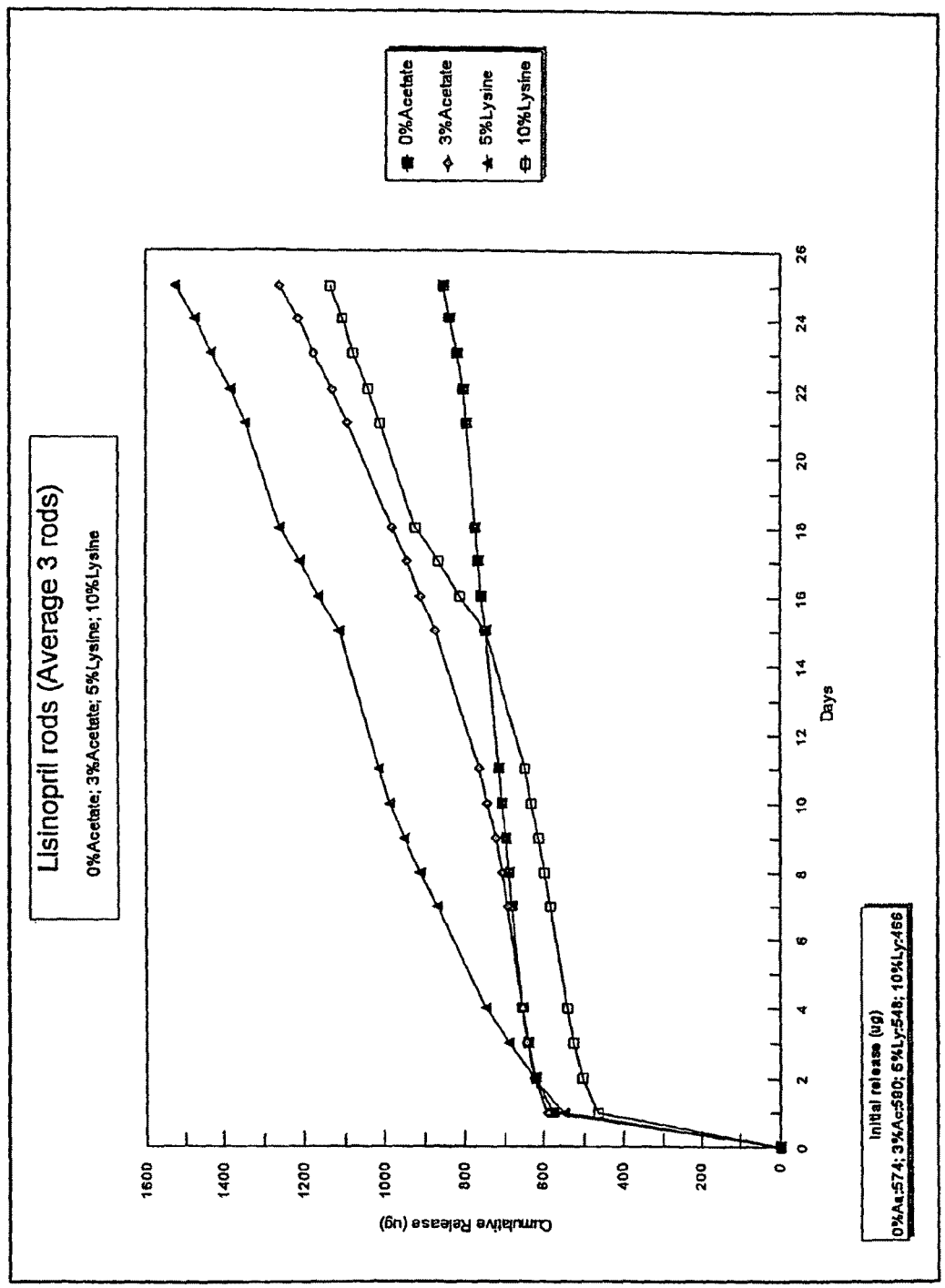

FIG. 7 provides a graph showing the average daily in vitro release profile from three 100 mg rods of each of formulations:

(XVII) 6% lisinopril, and balance stearin;
(XVIII) 6% lisinopril, 3% sodium acetate and balance stearin;
(XIX) 6% lisinopril, 5% lysine and balance stearin; and
(XX) 6% lisinopril, 10% lysine and balance stearin.

The graph demonstrates that following an initial rapid release (finished at about day 1) a sustained gradual release of lisinopril was achieved by all formulations over 25 days of testing, although the average daily release of this period of sustained release was low in the case of formulation XVII (i.e. with no sodium acetate or lysine).

Figure 8:
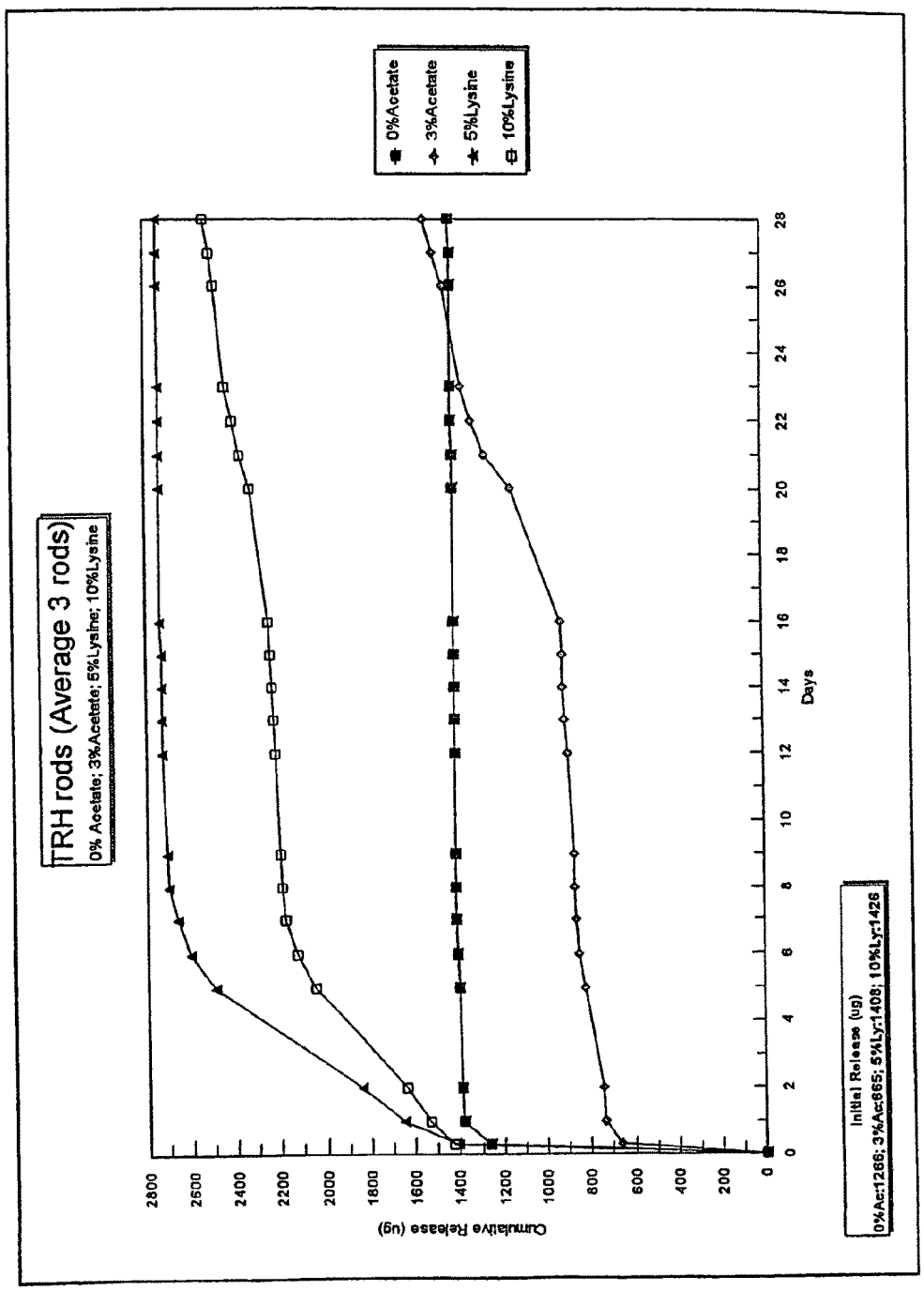

FIG. 8 provides a graph showing the average daily in vitro release profile from three 100 mg rods of each of formulations:

(XXI) 6% thyrotropin releasing hormone (TRH), and balance stearin;
(XXII) 6% thyrotropin releasing hormone (TRH), 3% sodium acetate and balance stearin;
(XXIII) 6% thyrotropin releasing hormone (TRH), 5% lysine and balance stearin; and
(XXIV) 6% thyrotropin releasing hormone (TRH), 10% lysine and balance stearin.

The graph demonstrates that following a very rapid initial release, a sustained gradual release of TRH was achieved with formulations XXII, XXIII and XXIV over the 28 day period of testing. Where no sodium acetate or lysine was included, no further TRH release was observed after day 1.

Figure 9:
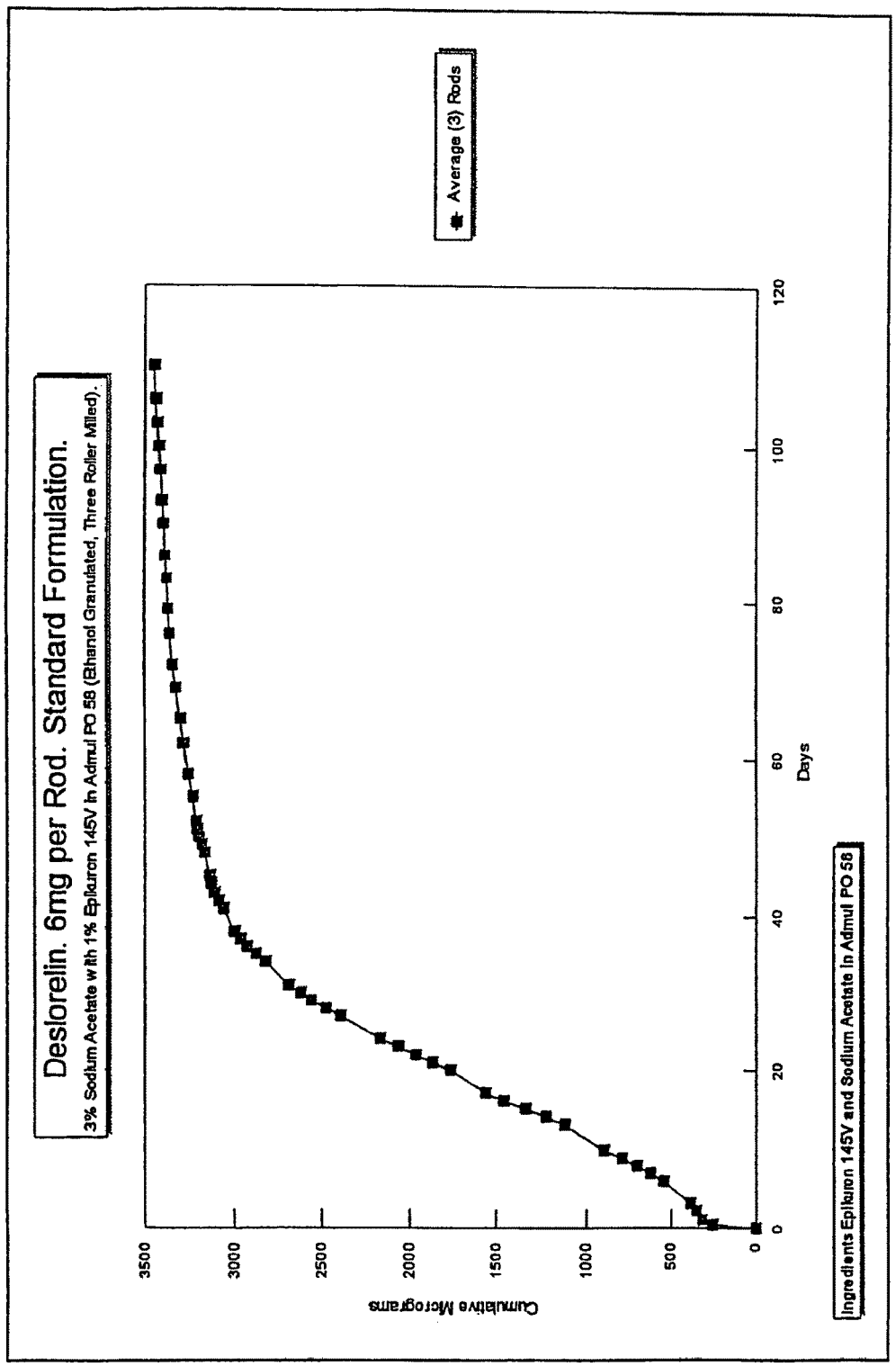

FIG. 9 provides a graph showing the average daily in vitro release profile from three 100 mg rods of formulation:

(XXV) 6% deslorelin, 3% sodium acetate and balance stearin.

The graph demonstrates that sustained release of deslorelin over 110 days was achieved.

Figure 10A:
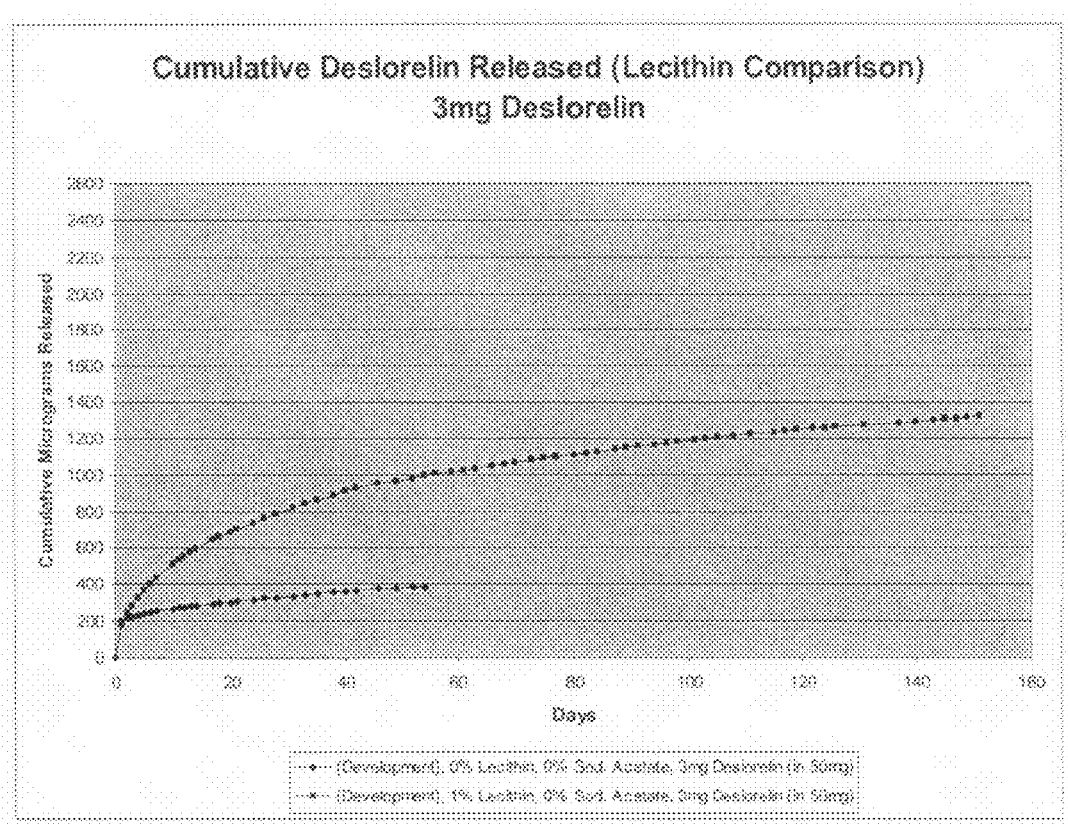
Figure 10B:
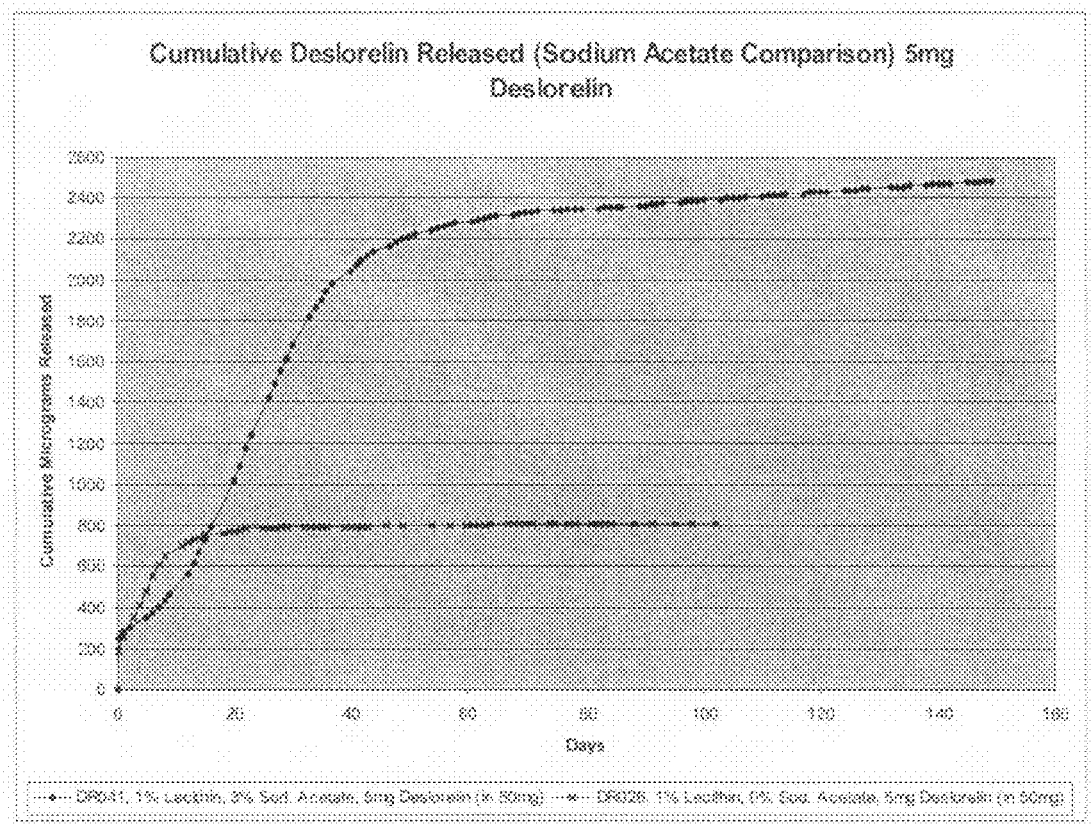

FIG. 10 provides graphs showing the average daily in vitro release profile from 50 mg rods of formulation:

(A)
(XXVI) 6% deslorelin, and balance stearin (i.e. 0% sodium acetate and 0% lecithin);
(XXVII) 6% deslorelin, 1% lecithin and balance stearin (i.e. 0% sodium acetate);
(B)
(XXVIII) 10% deslorelin, 1% lecithin and balance stearin (i.e. 0% sodium acetate);
(XXIX) 10% deslorelin, 3% sodium acetate, 1% lecithin and balance stearin;
(C)
(XXVIII) 10% deslorelin, 1% lecithin and balance stearin (i.e. 0% sodium acetate);
(XXIX) 10% deslorelin, 3% sodium acetate, 1% lecithin and balance stearin; and
(XXX) 10% deslorelin, 1.5% sodium acetate, 1% lecithin and balance stearin.

EXAMPLES

Formulations Comprising Deslorelin and Lecithin

Formulations I and II (detailed above) were prepared as follows:

Stearin (supplied as free flowing beads of 1 mm or less in diameter made by Quest International Pty Ltd (Netherlands) and lecithin were hand mixed using a spatula in a small beaker. Deslorelin (Bachem, Switzerland) pre-treated by the above described freeze drying process, was then added and thoroughly mixed into the excipients. The mixed material was transferred to the barrel of a ram extruder that has a 1 mm nozzle attached and is equilibrated to 55° C. The ram extrusion pressure was 40 psi. The ram was attached and pressure applied until the product began to extrude. At this point the pressure was backed off and the product allowed to reach 55° C. The product was then extruded at a rate of 3 g over a 30 second period. The resulting exudate was allowed to cool and then broken up and re-extruded through a 1 mm nozzle. This step was included to ensure uniformity of content throughout the matrix. The 1 mm nozzle was then replaced with a 2.3 mm diameter nozzle. The same product temperature equilibration procedure was conducted prior to extrusion. The product was then extruded and after cooling the long rods produced were sectioned into lengths of the required weight.

FIG. 1 provides results of in vitro deslorelin release with 100 mg rods containing 6 mg deslorelin. The assay involved immersing each rod into separate containers with 1 ml of phosphate buffered saline (PBS; as hereinbefore described) placed in a reciprocating water bath at 37° C. The PBS was replaced daily and the withdrawn PBS assayed for deslorelin with HPLC. The figure shows that after an initial rapid release of deslorelin, sustained release extending over a prolonged period (110 days) was achieved. The average daily rate of deslorelin release during the sustained release period was within the range 50-2 µg/day.

Formulations Comprising Deslorelin and Sodium Sulphate

Formulations III and IV were prepared with sodium sulphate (Ajax Chemicals, USA) in the same manner as described above for deslorelin/lecithin formulations.

FIG. 2 provides results of in vitro deslorelin release with 100 mg rods containing 6 mg deslorelin. The figure shows that a greater initial rapid release of deslorelin (534 µg vs. 438 µg) was achieved using a 5% concentration of sodium sulphate rather than a 2% concentration. After the initial rapid release (finished at about day 10), the rate of release was about 10-2 µg/day for the next 95 days for both formulations.

Formulations Comprising Deslorelin and HPMC

Formulations V and VI were prepared with hydroxy propyl methylcellulose (HPMC) in the same manner as described above for deslorelin/lecithin formulations.

FIG. 3 provides results of in vitro deslorelin release with 100 mg rods containing 6 mg deslorelin. The figure shows that a much greater initial rapid release of deslorelin (685 µg vs. 403 µg) was achieved using 5% HPMC rather than 2% HPMC. After the initial rapid release (finished at about day 10), the rate of release was about 10-2 µg/day for the next 95 days for both formulations.

Formulations Comprising Deslorelin and Glucose

Formulations VII and VIII were prepared with glucose (Ajax Chemicals, USA) in the same manner as described above for deslorelin/lecithin formulations.

FIG. 4 provides results of in vitro deslorelin release with 100 mg rods, containing 6 mg deslorelin. The figure shows that a much greater initial rapid release of deslorelin (790 µg vs. 403 µg) was achieved using 5% glucose rather than 2% glucose. After the initial rapid release (finished at about day 10), the rate of release was about 50-2 µg/day for the next 95 days for both formulations.

Formulations Comprising Somatostatin and Sodium Acetate or Lysine

Formulations IX to XII were prepared with sodium acetate or lysine in a manner similar to that described above for deslorelin/lecithin formulations. The somatostatin was obtained from Bachem (Switzerland).

FIG. 5 provides results of in vitro somatostatin release with 100 mg rods, containing 6 mg somatostatin. The figure shows that a greater initial rapid release of somatostatin was achieved using lysine than sodium acetate.

Formulations Comprising Naltrexone and Sodium Acetate or Lysine

Formulations XIII to XVI were prepared with sodium acetate or lysine in a manner similar to that described above for deslorelin/lecithin formulations.

FIG. 6 provides results of in vitro naltrexone release with 100 mg rods, containing 6 mg naltrexone. The figure shows that a sustained gradual release of naltrexone was achieved by all formulations over 23 days of testing, although the average daily release was low when no sodium acetate or lysine was included.

Formulations Comprising Lisinopril and Sodium Acetate or Lysine

Formulations XVII to XX were prepared with sodium acetate or lysine in a manner similar to that described above for deslorelin/lecithin formulations. The lisinopril was obtained from Sigma Chemical Co. (USA).

FIG. 7 provides results of in vitro lisinopril release from 100 mg rods, containing 6 mg lisinopril. The figure shows that following an initial rapid release (finished at about day 1) a sustained gradual release of lisinopril was achieved by all formulations over 25 days of testing, although the average daily release of this period of sustained release was low in the case of formulation XVII which contains no sodium acetate or lysine.

Formulations Comprising TRH and Sodium Acetate or Lysine

Formulations XXI to XXIV were prepared with sodium acetate or lysine in a manner similar to that described above for deslorelin/lecithin formulations. The TRH was obtained from Sigma Chemical Co (USA).

FIG. 8 provides results of in vitro TRH release from 100 mg rods, containing 6 mg TRH. The figure shows that following a very rapid initial release, a sustained gradual release of TRH was achieved with formulations XXII, XXIII and XXIV over the 28 day period of testing. Where no sodium acetate or lysine was included, no further TRH release was observed after day 1.

Formulations Comprising Deslorelin and Sodium Acetate

Formulation XXV were prepared with sodium acetate as the pore-forming agent in the same manner as described above for deslorelin/lecithin formulations.

FIG. 9 provides results of in vitro deslorelin release with 6 mg rods. The figure shows that sustained release of deslorelin over 110 days was achieved.

Formulations Comprising Deslorelin, Lecithin and Sodium Acetate

Solid formulations XXIX and XXX, in accordance with the present invention wherein the pore-forming agent comprises a combination of lecithin and sodium acetate, were prepared in a manner similar to that described above for deslorelin/lecithin formulations (i.e. Formulations I and II). Comparative formulations XXXVI-XXXVIII comprising lecithin (1% w/w) or deslorelin and stearin alone, were similarly prepared.

FIG. 10 shows that formulations XXVI with no lecithin and no sodium acetate, showed an initial "rapid" release during the first day of about 50% of the total amount of deslorelin eventually released by day 55. Addition of 1% lecithin to the formulation (formulation XXVII) did not change the initial release of the active agent but did increase the release of the active agent after day 1; release at day 55 was about 2.5 fold that in the absence of lecithin and the release of the active agent continued past day 140. Formulation XXVIII containing lecithin but no sodium acetate showed rapid release over about 8 days then further, slower, release to about day 20 with no further release of the active agent thereafter. The total amount of the active agent released from formulation XXVIII was about 800 µg. Unexpectedly, addition of 3% sodium acetate to produce formulation XXIX resulted in a slower rate of release between day 2 and about day 14 and dramatically enhanced the rate of release after day 15 to increase the total amount of the active agent released by about 3 fold to about 2400 µg.

Figure 10C:
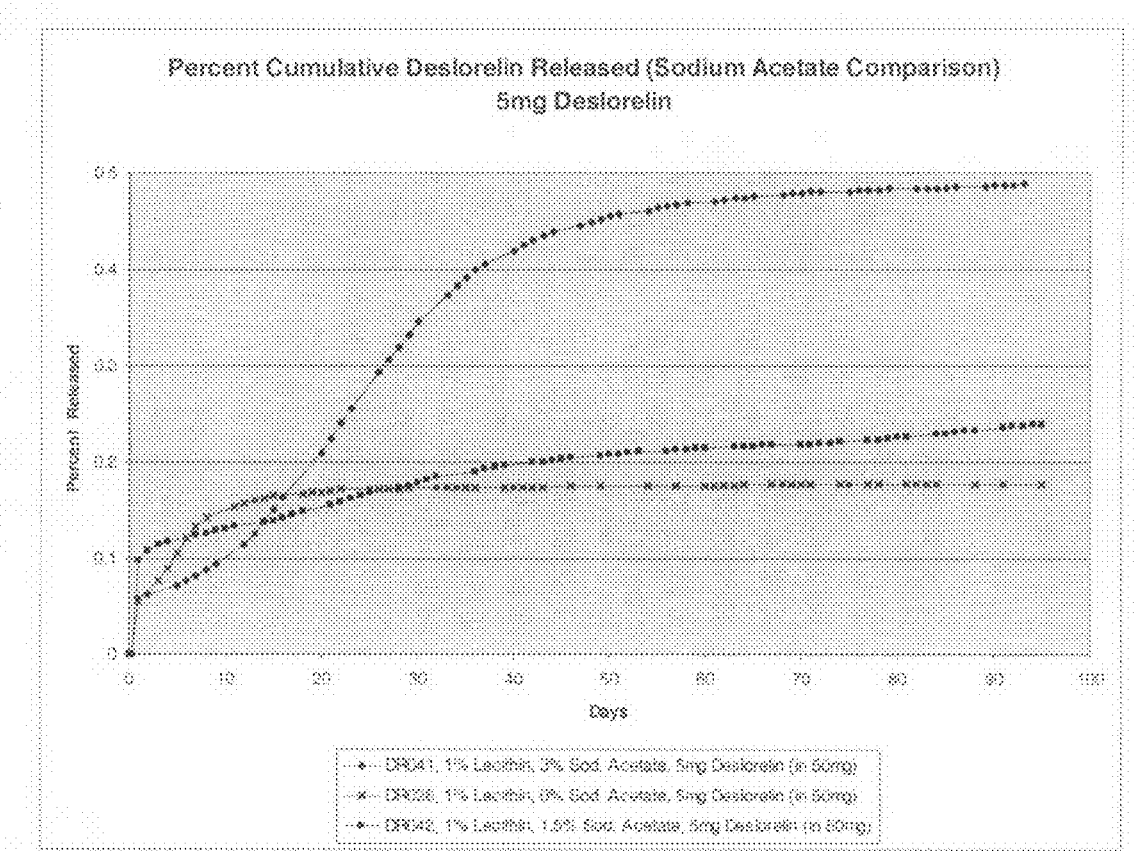

The relative significance of addition of sodium acetate to the formulation containing lecithin is depicted in FIG. 10C. Increasing the content of sodium acetate from 0 to 1.5% to 3% resulted in an increased number of days of release and an increase in the proportion of the total amount of the active agent released.

The results shown in FIG. 10 highlight that formulations which include a combination of lecithin and an organic salt as the pore-forming agent, offer a steadier rate of release of the active agent from the stearin excipient, and also achieve a greater level of total amount of active agent released, relative to formulations comprising lecithin or an organic salt alone. The steadier rate of release allows the preparation of formulations that perform in a more consistent manner, while the greater level of total amount of active agent release permits more efficient usage of costly active agents.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A pharmaceutical and/or veterinary formulation comprising about 2-30% (w/w) (on an active basis) of at least one active agent, about 0.5-20.0% (w/w) of a pore-forming agent comprising lecithin and an organic salt, and the balance stearin.

2. A formulation according to claim 1, wherein the formulation comprises about 5-10% (w/w) (on an active basis) of the at least one active agent, about 1.0-10.0% (w/w) of the pore forming agent, and the balance stearin.

3. A formulation according to claim 1, wherein the formulation comprises about 5-10% (w/w) (on an active basis) of the at least one active agent, about 2.0-5.0% (w/w) of the pore-forming agent, and the balance stearin.

4. A formulation according to claim 1, wherein the organic salt is sodium acetate.

5. A formulation according to claim 2, wherein the organic salt is sodium acetate.

6. A formulation according to claim 3, wherein the organic salt is sodium acetate.

7. A formulation according to claim 1, wherein the at least one active agent is/are not a nucleic acid compound or derivative.

8. A formulation according to claim 1, wherein the at least one active agent is selected from the group consisting of peptides, polypeptides and proteins.

9. A formulation according to claim 1, wherein the at least one active agent is selected from the group consisting of lipid lowering agents, cyclosporins, angiotensin converting enzyme inhibitors, painkilling agents, opioid antagonists, antidepressant agents, non-steroidal anti-inflammatory agents, paroxetine, and theophylline and theophylline analogues.

10. A formulation according to claim 1, wherein the at least one active agent is selected from GnRH agonists.

11. A formulation according to claim 10, wherein the GnRH agonist(s) is selected from deslorelin, eulexin, goserelin, leuprolide, dioxalan derivatives, triptorelin, mieterelin, buserelin, histerlin, nafarelin, lutrelm, leuprorelin and LHRH analogues.

12. A formulation according to claim 10, wherein the GnRH agonist is deslorelin and the organic salt is sodium acetate.

13. A formulation according to claim 10, wherein the GnRH agonist is deslorelin and the pore-forming agent consists of lecithin and sodium acetate.

14. A formulation according to claim 1, wherein the at least one active agent has/have a log octanol/water partition coefficient (log P) in the range of 5.0 to −3.0.

15. A formulation according to claim 14, wherein the at least one active agent has/have a log octanol/water partition coefficient (log P) in the range 1.0 to −3.0.

16. A formulation according to claim 1, wherein the formulation is in the form of free flowing beads or rods.

17. A method of treating a disease or condition in a human or other animal, the method comprising administering to the human or other animal a formulation according to claim 1.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: 3-[5-oxo-L-prolyl]
<220> FEATURE:
<221> NAME/KEY: MOD_RES
<222> LOCATION: (5)
<223> OTHER INFORMATION: D-Ser(t butyl)
<220> FEATURE:
<221> NAME/KEY: MOD_RES
<222> LOCATION: (9)
<223> OTHER INFORMATION: Azgly

<400> SEQUENCE: 1

Xaa Trp Ser Tyr Xaa Leu Arg Pro Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: pGlu
<220> FEATURE:
<221> NAME/KEY: MOD_RES
<222> LOCATION: (6)
<223> OTHER INFORMATION: D-Trp
<220> FEATURE:
<221> NAME/KEY: MOD_RES
<222> LOCATION: (9)
<223> OTHER INFORMATION: Pro-ethylamide

<400> SEQUENCE: 2

Xaa His Trp Ser Tyr Xaa Leu Arg Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: 5-oxo-L-prolyl
<220> FEATURE:
<221> NAME/KEY: MOD_RES
<222> LOCATION: (6)
<223> OTHER INFORMATION: D-Leu
<220> FEATURE:
<221> NAME/KEY: MOD_RES
<222> LOCATION: (8)
<223> OTHER INFORMATION: N-ethyl-L-prolinamide acetate

<400> SEQUENCE: 3

Xaa His Trp Ser Tyr Xaa Arg Xaa
```

```
1               5
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: 5-oxo-L-prolyl
<220> FEATURE:
<221> NAME/KEY: MOD_RES
<222> LOCATION: (6)
<223> OTHER INFORMATION: D-Trp
<220> FEATURE:
<221> NAME/KEY: MOD_RES
<222> LOCATION: (10)
<223> OTHER INFORMATION: glycinamide

<400> SEQUENCE: 4

```
Xaa His Trp Ser Tyr Xaa Leu Arg Pro Xaa
1               5                   10
```

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: pGlu
<220> FEATURE:
<221> NAME/KEY: MOD_RES
<222> LOCATION: (6)
<223> OTHER INFORMATION: 2-methyl-D-Trp
<220> FEATURE:
<221> NAME/KEY: MOD_RES
<222> LOCATION: (9)
<223> OTHER INFORMATION: Pro-ethylamide

<400> SEQUENCE: 5

```
Xaa His Trp Ser Tyr Xaa Leu Arg Xaa
1               5
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: oxo-L-prolyl
<220> FEATURE:
<221> NAME/KEY: MOD_RES
<222> LOCATION: (6)
<223> OTHER INFORMATION: D-Ser(t butyl)
<220> FEATURE:
<221> NAME/KEY: MOD_RES
<222> LOCATION: (9)
<223> OTHER INFORMATION: N-ethyl-L-prolinamide acetate

<400> SEQUENCE: 6

```
Xaa His Trp Ser Tyr Xaa Leu Arg Xaa
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (7)
<223> OTHER INFORMATION: D-(N-benzyl)His
<220> FEATURE:
<221> NAME/KEY: MOD_RES
<222> LOCATION: (9)
<223> OTHER INFORMATION: Pro-N-ethylamide

<400> SEQUENCE: 7

Pro His Trp Ser Tyr Leu Xaa Arg Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      GnRH agonist
<220> FEATURE:
<221> NAME/KEY: MOD_RES
<222> LOCATION: (1)
<223> OTHER INFORMATION: oxo-L-Pro
<220> FEATURE:
<221> NAME/KEY: MOD_RES
<222> LOCATION: (6)
<223> OTHER INFORMATION: 3-(2-naphthyl)-D-Ala
<220> FEATURE:
<221> NAME/KEY: MOD_RES
<222> LOCATION: (9)
<223> OTHER INFORMATION: N-ethyl-L-prolyl
<220> FEATURE:
<221> NAME/KEY: MOD_RES
<222> LOCATION: (10)
<223> OTHER INFORMATION: glycinamide acetate

<400> SEQUENCE: 8

Xaa His Trp Ser Tyr Xaa Leu Arg Xaa Xaa
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 9

Pro Gln Gln Phe Phe Gly Leu Met
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 10
```

```
Gln Gln Phe Phe Gly Leu Met
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 11

Gln Phe Phe Gly Leu Met
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 12

Phe Phe Gly Leu Met
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 13

Phe Gly Leu Met
1

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      substance P antagonist
<220> FEATURE:
<223> OTHER INFORMATION: C-term amidated

<400> SEQUENCE: 14

Gly Leu Met
1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      galanin fragment peptide

<400> SEQUENCE: 15

Pro Pro Ala Leu Ala Leu Ala
```

```
<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      thyrotropin releasing hormone analogue
<220> FEATURE:
<221> NAME/KEY: MOD_RES
<222> LOCATION: (1)
<223> OTHER INFORMATION: pGlu

<400> SEQUENCE: 16

Xaa His Pro Gly
1
```